United States Patent
Dal Farra et al.

(10) Patent No.: US 8,450,456 B2
(45) Date of Patent: May 28, 2013

(54) ACTIVATING PEPTIDE OF THE SYNTHESIS OF AQUAPORINS AND COSMETIC AND/OR PHARMACEUTICAL COMPOSITION CONTAINING IT

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 262 days.

(21) Appl. No.: 12/808,266

(22) PCT Filed: Dec. 17, 2008

(86) PCT No.: PCT/FR2008/001759
§ 371 (c)(1),
(2), (4) Date: Jun. 15, 2010

(87) PCT Pub. No.: WO2009/112645
PCT Pub. Date: Sep. 17, 2009

(65) Prior Publication Data
US 2010/0261658 A1    Oct. 14, 2010

(30) Foreign Application Priority Data
Dec. 21, 2007   (FR) ...................................... 07 08977

(51) Int. Cl.
*C07K 5/10*   (2006.01)
(52) U.S. Cl.
USPC .......... 530/330; 530/329; 530/331; 514/18.6; 514/18.8
(58) Field of Classification Search
USPC ................. 530/330, 329, 331; 514/18.6, 18.8
See application file for complete search history.

(56) References Cited

FOREIGN PATENT DOCUMENTS

| | | |
|---|---|---|
| FR | 2801504 | 6/2001 |
| FR | 2831058 | 4/2003 |
| FR | 2874502 | 3/2006 |
| JP | 08-245694 | 9/1996 |
| WO | 92/03147 | 3/1992 |

OTHER PUBLICATIONS

Cao, C. et al., "EGFR-mediated expression of aquaporin-3 is involved in human skin fibroblast migration," *Biochem. J.*, 400, pp. 225-234 (2006).
Deen, P.M.T. et al., "Requirement of Human Renal Water Channel Aquaporin-2 for Vasopressin-Dependent Concentration of Urine," *Science*, vol. 264, pp. 92-95 (Apr. 1, 1994).
Kawedia, J.D. et al., "Interaction between transcellular and paracellular water transport pathways through Aquaprin 5 and the tight junction complex," *PNAS*, Vo. 104, No. 9, pp. 3621-3626 (Feb. 27, 2007).
Kullman, W., "Proteases as Catalysts for Enzymic Syntheses of Opioid Peptides," *The Journal of Biological Chemistry*, vol. 255, No. 17, pp. 8234-8238 (Sep. 10, 1980).
Ma, T., et al., "Impaired Stratum Corneum Hydration in Mice Lacking Epidermal Water Channel Aquaporin-3," *The Journal of Biological Chemistry*, vol. 277, No. 19, pp. 17147-17153 (May 10, 2002).
Sougrat, R. et al., "Functional Expression of AQP3 in Human Skin Epidermis and Reconstructed Epidermis," *The Journal of Investigative Dermatology*, vol. 118, No. 4, pp. 678-685 (Apr. 2002).
PCT, International Search Report, International Application No. PCT/FR2008/001759; 6 pages (mailed Aug. 27, 2009, published Sep. 17, 2009).
Database Registry, American Chemical Society; Peptide Pro-Ala. Arg (RN No. 480543-38-2); 1 page (Jan. 23, 2003).
Dumas et al., "Hydrating skin by stimulating biosynthesis of aquaporins," Journal of Drugs in Determatolory, New York, Vol. Supplement, No. 6, pp. 20-24 (Jun. 1, 2006).

*Primary Examiner* — David Lukton
(74) *Attorney, Agent, or Firm* — Thompson Hine L.L.P.

(57) ABSTRACT

The present invention concerns a peptide of the general formula (I):
$R_1\text{-}(AA)_n\text{-}X_1\text{—}X_2\text{—}X_3\text{-Pro-}X_4\text{—}X_5\text{—}X_7\text{-}(AA)_p\text{-}R_2$,
capable of activating the synthesis of proteins of the family of aquaporins.
The present invention also concerns a cosmetic, nutraceutical or pharmaceutical composition, comprising a peptide of general formula (I) as active principle. The invention also relates to the use of this new active principle in a cosmetic or nutraceutical composition, intended to improve the moisturizing and the barrier function of the epidermis and intended to stimulate cutaneous regeneration. The invention also relates to the use of this new active principle to realize a pharmaceutical composition, and in particular a dermatological composition, intended to regulate and/or stimulate the activity of the aquaporins and to thus treat the pathological dryness of the skin or mucosa. The invention also relates to a method of cosmetic treatment intended to prevent or combat against dryness of the skin and mucosa, and the manifestations of cutaneous ageing.

21 Claims, No Drawings

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Ser Met Asn Pro Gly Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Gln Pro Ala Lys Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Asn Pro Ala Arg Asp
1               5

<210> SEQ ID NO 4
<211> LENGTH: 4
<212> TYPE: PRT
<213> ORGANISM: Artificial Sequence
```

```
<220> FEATURE:
<223> OTHER INFORMATION: Synthetic peptide

<400> SEQUENCE: 4

Asn Pro Ala Arg
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 5

Asn Pro Ala Arg
1

<210> SEQ ID NO 6
<211> LENGTH: 3
<212> TYPE: PRT
<213> ORGANISM: Artificial Sequence
<220> FEATURE:
<223> OTHER INFORMATION: Synthetic peptide

<400> SEQUENCE: 6

Asn Pro Ala
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION

<400> SEQUENCE: 7

Asn Pro Ala
1

<210> SEQ ID NO 8
<211> LENGTH: 3
<212> TYPE: PRT
<213> ORGANISM: Artificial Sequence
<220> FEATURE:
<223> OTHER INFORMATION: Synthetic peptide

<400> SEQUENCE: 8

Pro Ala Arg
1

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: AMIDATION
```

```
<400> SEQUENCE: 9

Pro Ala Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide

<400> SEQUENCE: 10

Leu Asn Pro Ala
1
```

ACTIVATING PEPTIDE OF THE SYNTHESIS OF AQUAPORINS AND COSMETIC AND/OR PHARMACEUTICAL COMPOSITION CONTAINING IT

This application is a 371 of PCT/FR2008/001759, filed Dec. 17, 2008, which claims foreign priority to FR 0708977, filed Dec. 21, 2007.

The present invention lies in the cosmetic and pharmaceutical field, and more particularly in the field of dermatology. The present invention concerns a peptide capable of activating the synthesis of proteins of the family of aquaporins, of the general formula (I): $R_1\text{-}(AA)_n\text{-}X_1\text{---}X_2\text{---}X_3\text{-Pro-}X_4\text{---}X_5\text{---}X_7\text{-}(AA)_p\text{-}R_2$.

The present invention likewise concerns a cosmetic, nutraceutical or pharmaceutical composition, and particularly a dermatological composition, comprising at least one peptide of the general formula (I), as active principle, alone or in association with at least one other active principle. The invention likewise relates to the use of this new active principle, orally or topically, in a cosmetic or nutraceutical composition intended to improve the moisturizing and the barrier function of the epidermis, and to stimulate cutaneous regeneration. The invention likewise relates to the use of this new active principle, orally or topically, to produce a pharmaceutical composition, and in particular a dermatological composition, intended to regulate and/or stimulate the activity of the aquaporins and to thus treat the pathologies involving a pathological dryness of the skin or the mucosa, such as xerosis or eczema, the symptoms of a dry mouth or dryness of the eye. The invention further deals with a method of cosmetic treatment intended to prevent or combat against dryness of the skin and of the mucosa and the manifestations of cutaneous ageing, according to which an effective quantity of peptide capable of activating the synthesis of the aquaporins, or a composition containing it, is applied on the areas which are to be treated.

The skin is a vital organ composed of several layers (dermis, proliferative layers and stratum corneum) which covers the entire surface of the body and ensures essentially a barrier function with respect to the exterior environment. This barrier function is based in particular on the quality of the epidermis, which depends in particular on the state of the stratum corneum and on the balance between the proliferation and the differentiation of the epidermal keratinocytes. The quality and good functioning of the skin are closely linked to the water content of the different layers of the epidermis. Thus, in a normal epidermis, the proliferative layers contain approximately 70% water, whereas the stratum corneum contains only 10 to 15%.

The moisturizing of the stratum corneum is the result of three factors: the supply of water from the dermis, the loss of water towards the exterior environment and the capacity of the stratum corneum to fix the water molecules.

The regulation of the distribution of water is carried out by hormones (aldosterone, sex hormones), the pH or the osmotic variations. The cellular membranes are hydrophobic in nature and are therefore not very permeable to water, but water channels exist, types of pores facilitating the passage of water and certain solutions.

Aquaporins are a class of transmembrane proteins transporting water and small molecules in solution, such as glycerol and urea, which facilitate the transport of water in the epithelia and endothelia.

The determinant function of aquaporins in the epithelia involved in the transport of water or solvents, such as the kidney, have been well studied (Deen et al., 1994). Likewise, aquaporins have been rapidly identified in the exocrine glands producing saliva or tears. However, the discovery of type 3 aquaporins, or AQP3, in the human epidermis, and more precisely in the plasmic membrane of the keratinocytes of the proliferative layers of the epidermis (SOUGRAT R. et al., J. Invest. Dermatol., 2002), has brought to light the importance of the regulated hydric flows in the skin. AQP3-s are capable of transporting water and glycerol, the latter playing an important part in the constitution of the hydrolipidic surface film and also in maintaining the flexibility and the sensory qualities of the stratum corneum.

The importance of the AQP3s has been demonstrated in the mouse. In fact, the inactivation of the gene causes the appearance of multiple deficiencies of the skin, such as a low level of moisturizing, an inefficient barrier function, an increased period of tissue regeneration and a reduction in elasticity (Ma T. et al., J. Biol. Chem., 277, 2002). It has been discovered since that aquaporin 3 is expressed in the dermal fibroblasts where it is involved in the migration of these cells during the regeneration of wounds (Cao C. et al., Biochem J., 2006). Moreover, the aquaporins play a part in the barrier function by positively regulating the establishing of cellular links and communications of the tight junction type (KAwedia J. et al., PNAS 104(9), 2007).

The moisturizing and the AQP3 content of the keratinocytes are closely linked. Thus, the increasing of AQP3 in the skin causes a better moisturizing of the epidermis (Dumas M., J. Drugs Dermatol., Jun. 6, 2007).

The cutaneous losses of water can have several origins: hereditary, acquired or linked to the environment. In a very dry environment, the losses of water by evaporation from the stratum corneum are significant and can exceed the rate of replacement by transcellular diffusion.

In the course of cutaneous ageing, the skin becomes dry. Thus, in old subjects, and in particular those over 50 years of age, the manifestation of xerosis or a dryness of the mucosa is very often observed, linked to less secretion of sebum, hormonal changes or slowing down of the hydric flow through the epidermis. The skin is therefore the seat of itching and pulling, two characteristic symptoms of a dry skin. Among the acquired pathologies expressed by a dryness of the skin, xerosis can be mentioned, induced by photochemotherapy, and eczema. Among the acquired pathologies causing a dryness of the mouth, or xerostomia, Sjogren's syndrome can be mentioned, or radiation of the neck. Pathological dryness can likewise affect other mucous areas of the organism, among which the vaginal mucosa and the ocular mucosa can be mentioned.

A first alternative for the treatment of dry skin consists in topically administering products intended to restore the cutaneous barrier, such as humectant agents capable of fixing water, among which can be mentioned urea and lactic acid, which enter in the composition of the NMF (Natural Moisturizer Factor; proteolytic derivatives of filaggrin), filmogenic agents intended to retain water, or else agents capable of reconstructing the cutaneous barrier (squalenes, fatty acid ceramides). However, these products have a superficial action which does not correct the biological defects of a skin suffering from chronic dehydration.

In this context, the particular properties of aquaporins make them possible biological targets for improving the moisturizing of the skin and reducing the signs of cutaneous dryness. Thus, the patent FR 2 801 504 describes the increase of AQP3 in the skin by an extract of *Ajuga turkestanica* plants, and allowed the moisturizing of the skin to be improved. An extract of pomegranate has, elsewhere, been described as active principle, able to be used orally and topically, to stimulate the activity of aquaporins and to regulate the movements of water and glycerol in the tissues (FR 2 874 502). However, to date, no peptide capable of activating the aquaporins, as disclosed in the present invention, has yet been described.

The main aim of the present invention is to provide a new active principle capable of preventing and combating against dryness of the skin and of the mucosa and the manifestations of cutaneous ageing. The inventors have in fact demonstrated a biological activity which is able to be used in the cosmetic and therapeutic field, in particular the dermatological field, of peptides capable of activating the synthesis of aquaporins.

It has been demonstrated in particular that these peptides, when they are applied on the skin, improve the moisturization and the barrier function of the epidermis and the mucosa, and stimulate cutaneous regeneration. These properties have been demonstrated by a protection of the cutaneous tissue and a reduction to apoptosis following a hydric stress.

"Active principle capable of preventing and combating against dryness of the skin and of the mucosa and the manifestations of cutaneous ageing" is understood to mean any substance capable of improving the moisturizing and the barrier function of the epidermis and of the mucosa, or of reducing the apoptosis in cells or tissues subjected to a hydric stress.

"Topical application" is understood to mean the fact of applying or spreading the active principle according to the invention, or a composition containing it, on the surface of the skin or of a mucosa.

"Cosmetically or dermatologically acceptable" means that the active principle according to the invention, or a composition containing it, is suitable for coming in contact with the skin or a mucosa without causing reactions of toxicity or intolerance.

"Nutraceutical" is understood to mean a skin care method which involves the administration of active principles by ways other than topically, to subjects in good health who wish to improve or maintain their physical appearance.

Thus, the first object of the invention is a peptide capable of activating the synthesis of aquaporins, as active principle, alone or in association with at least one other active principle.

"Active principle capable of activating the synthesis of aquaporins" is understood to mean any peptide or biologically active derivative capable of increasing the activity of the aquaporins, either by increasing the proteic synthesis of the aquaporin (by direct or indirect modulation of the genic expression of the aquaporin), or by increasing the biochemical activity of the aquaporin, either by other biological processes such as the stabilisation of the aquaporin protein or also the stabilisation of the RNA messenger transcripts.

Preferably, according to the present invention, the said peptide capable of activating the aquaporin, or its biologically active derivative, is a peptide wherein the number of amino acids is comprised between 2 and 15.

Preferably, according to the present invention, the aquaporin will be aquaporin 3, or AQP3, present in the membranes of the keratinocytes.

The expression "biologically active" means "which has an in vivo or in vitro activity which is characteristic of the activity of the active principle according to the invention".

According to a particularly advantageous embodiment of the invention, the peptide has a sequence that answers in whole or in part with the general formula (I)

$R_1$-(AA)$_n$-$X_1$—$X_2$—$X_3$-Pro-$X_4$—$X_5$—$X_7$-(AA)$_p$-$R_2$ in which
$X_1$ is serine or no amino acid,
$X_2$ is methionine or leucine or no amino acid,
$X_3$ is asparagine or glutamine or no amino acid,
$X_4$ is alanine or glycine,
$X_5$ is arginine or lysine or no amino acid,
$X_6$ is serine, aspartic acid or no amino acid AA represents any amino acid, or one of its derivatives, and n and p are integers comprised between 0 and 4, $R_1$ represents the primary amine function of the N-terminal amino acid, free or substituted by a protective group which may be chosen from an acetyl group, a benzoyl group, a tosyl group or a benzoyloxycarbonyl group, $R_2$ represents the hydroxyl group of the carboxyl function of the C-terminal amino acid, free or substituted by a protective group which may be chosen from an alkyl chain of $C_1$ to $C_{20}$, or a NH2, NHY or NYY group with Y representing an alkyl chain of $C_1$ to $C_4$.

According to a quite particularly preferred embodiment of the invention, the biologically active peptide has the sequence:

```
(SEQ ID n°1)     Ser-Met-Asn-Pro-Gly-Arg (SEQ ID n°2)     Gln-Pro-Ala-Lys-Ser (SEQ ID n°3)     Asn-Pro-Ala-Arg-Asp (SEQ ID n°4)     Asn-Pro-Ala-Arg (SEQ ID n°5)     Asn-Pro-Ala-Arg-NH₂

(SEQ ID n°6)     Asn-Pro-Ala (SEQ ID n°7)     Asn-Pro-Ala-NH₂

(SEQ ID n°8)     Pro-Ala-Arg (SEQ ID n°9)     Pro-Ala-Arg-NH₂

(SEQ ID n°10)    Leu-Asn-Pro-Ala
```

According to a particularly interesting embodiment, the biologically active peptide corresponds to the sequence SEQ ID No4.

According to another particularly interesting embodiment, the biologically active peptide corresponds to the sequence SEQ ID no5.

The invention also concerns homologous forms of these sequences. The term "homologous" designates, according to the invention, any peptidic sequence identical to at least 50%, or preferably at least 80%, and even more preferably at least 90% of the said peptidic sequence, selected from the sequences SEQ ID no 1 to SEQ ID no 10. "Peptidic sequence identical to at least X %" is understood to designate a percentage of identity between the amino acid residues of the two sequences which are to be compared, obtained after the optimum alignment of the two sequences. The optimum alignment is obtained by means of algorithms of local homologies, such as those used by the IT software BLAST P or T BLAST N available on the NCBL site.

The term "homologous" can likewise designate a peptide which differs from the sequence of a peptide of sequence SEQ ID no 1 to SEQ ID no 10 by the substitution of chemically equivalent amino acids, i.e. by the substitution of one residue by another having the same characteristics. Thus, the conventional substitutions are made between Ala, Val, Leu and Ile; between Ser and Thr; between the acid residues Asp and Glu; between Asn and Gln; and between the basic residues Lys and Arg; or between the aromatic residues Phe and Tyr.

In the invention, the term "amino acid" refers here to any natural or non-natural organic acid having the formula:

—NHR—CR—C(O)—O— where each —R is independently selected between a hydrogen and an alkyl group having between 1 and 12 carbon atoms. Preferably, at least one —R group of each amino acid is a hydrogen. The term "alkyl" is understood to mean here a carbon chain, able to be linear or branched, substituted (mono- or poly-) or non-substituted; saturated, mono-saturated (a double or triple bond in the chain) or poly-unsaturated (two or more double bonds, two or more triple bonds, one or more double bonds or one or more triple bonds in the chain).

The term "peptide" designates a sequence of two or more amino acids linked between them by peptide bonds or by modified peptide bonds.

"Peptide" must be understood to mean the natural or synthetic peptide of the invention as described above, or at least one of its fragments, whether it is obtained by proteolysis or synthetically, or also any natural or synthetic peptide, the sequence of which is totally or partially constituted by the sequence of the previously described peptide. So as to improve the resistance to degradation, it can be necessary to use a protected form of the peptide according to the invention. The form of protection must obviously be a form which is biologically compatible and must be compatible with use in the field of cosmetics or pharmacy.

Numerous biologically compatible forms of protection can be envisaged. They are well known to the man skilled in the art such as, for example, the acylation or acetylation of the amino-terminal end, or the amidation or esterification of the carboxy-terminal end. Thus, the invention concerns a composition as previously defined, characterized by the fact that the peptide of sequence SEQ ID no1 to SEQ ID no10 is in protected or non-protected form. A protection can be used based on a substitution on the amino-terminal end by an acetyl group, a benzoyl group, a tosyl group or a benzoyloxy-carbonyl group. Preferably a protection is used based on the amidation of the hydroxyl function of the carboxy-terminal end by a NYY group with Y representing an alkyl chain of $C_1$ to $C_4$, or the esterification by an alkyl group. It is likewise possible to protect the two ends of the peptide.

The derivatives of peptides also concern the amino acids and the peptides linked between each other by a pseudo-peptidic bond. A "pseudo-peptidic bond" is understood to mean all the types of bonds capable of replacing the "conventional" peptidic bonds.

In the field of amino acids, the molecules have a geometry such that they can theoretically present themselves in the form of different optical isomers. Thus, a molecular conformation exists of the amino acid (AA) which deviates to the right the plane of polarization of light (dextrogyre conformation or D-aa), and a molecular conformation of the amino acid (aa) which deviates to the left the plane of polarization of light (levorotatory conformation or L-aa). The natural amino acids are always of levorotatoryconformation, consequently a peptide of natural origin will only be constituted by amino acids of the type L-aa. However, the chemical synthesis in the laboratory allows amino acids to be prepared having the two possible conformations. From this base material, it is thus possible to incorporate during the peptide synthesis both amino acids in the form of dextrogyre and levogyre optical isomers. Thus, the amino acids constituting the peptide according to the invention can be in the configuration L- and D-; preferably, the amino acids are in the L form. The peptide according to the invention can therefore in the form L-, D- or DL-.

The peptide of general formula (I) according to the invention can be obtained either by conventional chemical synthesis (in solid phase or in homogenous liquid phase), or by enzymatic synthesis (Kullman et al., J. Biol. Chem. 1980, 225, 8234), from constitutive amino acids or their derivatives.

The peptide according to the invention can likewise be obtained by fermentation of a strain of bacteria, modified or not, by genetic engineering, or also by extraction of proteins of animal or plant origin, preferably of plant origin, followed by a controlled hydrolysis which releases peptidic fragments corresponding in whole or in part to the peptides of general formula (I).

Very many proteins found in plants are liable to contain these sequences in the core of their structure. Managed hydrolysis allows these peptidic fragments to be released. It is possible, but not necessary for realizing the invention, to extract either the proteins concerned first of all and to then hydrolyse them, or to carry out the hydrolysis first of all on a crude extract and to then purify the peptidic fragments. It is likewise possible to use certain hydrolysed extracts without purifying the peptidic fragments thereof corresponding to the peptides of general formula I according to the invention, but nevertheless ensuring the presence of the said fragments by suitable analytical means.

Other simpler or more complex methods can be envisaged by the man skilled in the art knowing the art of synthesis, extraction and purification of proteins and peptides. Thus, the peptide according to the invention can be of natural or synthetic origin. Preferably according to the invention, the peptide is obtained by chemical synthesis.

According to the invention, the active principle can be a single peptide, a mixture of peptides or of peptidic derivatives and/or constituted by derivatives of amino acids.

According to an advantageous embodiment of the invention, the active principle according to the invention is previously solubilised in one or more cosmetically or pharmaceutically acceptable solvents, conventionally used by the man skilled in the art, such as water, glycerol, ethanol, propylene glycol, butylene glycol, dipropylene glycol, ethoxylated or propoxylated diglycols, cyclic polyols, petroleum jelly, a vegetable oil or any mixture of these solvents.

According to a further advantageous embodiment of the invention, the active principle according to the invention is previously solubilised in a cosmetic or pharmaceutical vector such as the liposomes, or adsorbed on pulverulent organic polymers, mineral supports such as talcs and bentonites, and more generally solubilised in, or fixed on, any cosmetically or pharmaceutically acceptable vector.

The second object of the invention is a cosmetic, nutraceutical or pharmaceutical composition, and in particular a dermatological composition, comprising, in a physiologically acceptable medium, an effective quantity of peptide capable of activating the synthesis of aquaporins, as active principle, alone or in association with at least one other active principle, as previously defined.

It is readily obvious that the invention is addressed to mammals in general, and more particularly to human beings.

The effective quantity of active principle corresponds to the quantity necessary to obtain the result which is sought, namely, to improve the moisturizing and the barrier function of the epidermis, and/or to stimulate cutaneous regeneration, and/or to regulate or to stimulate the activity of aquaporins, and/or to prevent or combat against dryness of the skin and of the mucosa, and the manifestations of cutaneous ageing.

According to an advantageous embodiment of the invention, the active principle according to the invention is present in the compositions of the invention at a concentration comprised between 0.0005 and 500 ppm (parts per million) approximately, and preferably at a concentration comprised between 0.01 and 5 ppm approximately with respect to the total weight of the final composition.

The composition which is able to be used according to the invention can consist in particular of a composition for hair care, and in particular a shampoo, a conditioner, a treatment lotion, cream or a hairdressing gel, a restructuring lotion for the hair, a mask, etc. The cosmetic composition according to the invention can be used in particular in treatments implementing an application which is followed, or not, by a rinsing, or again in the form of a shampoo. Thus, the active principle according to the invention will be able to be used advantageously in anti-dandruff care of the scalp.

It can likewise present itself in the form of a dye or mascara to be applied by a brush or a comb, in particular on the eyelashes, the eyebrows or the hair.

It is readily understood that the active principle according to the invention can be used alone or else in association with at least one other active principle, in a cosmetic or nutraceutical composition, or for the preparation of a pharmaceutical and/or dermatological composition.

Advantageously, the compositions which are able to be used according to the invention further contain various moisturizing active agents intended, in particular, for the prevention and/or treatment of disorders linked to ageing. Thus, the composition according to the invention can associate glycerol, as active adjuvant agent, to the active agent described in the present invention. This association is particularly advantageous and obtains an optimum moisturizing effectiveness, compared with the use of glycerol alone.

The compositions according to the invention will be able to be applied by any suitable way, in particular orally, parentally or externally topically, and their formulation will be adapted by the man skilled in the art, in particular for cosmetic or dermatological compositions. Advantageously, the compositions according to the invention are intended for an administration in a topical cutaneous manner. These compositions must therefore contain a cosmetically and/or dermatologically acceptable medium, i.e. compatible with the skin and the skin appendages and cover all the cosmetic or dermatological forms. These compositions will be able to be in particular in the form of creams, oil-in-water or water-in-oil or multiple emulsions, solutions, suspensions, gels, milks, lotions, sticks or else powders and suited to an application on the skin, the lips and/or the skin appendages. These compositions comprise the excipients necessary for their formulation, such as solvents, thickeners, diluents, surfactants, anti-oxidants, colorants, preservatives, parfums.

According to another form of the invention, the compositions will be suited to an oral administration for a pharmaceutical or nutraceutical usage. Thus, the compositions will be able to present themselves in particular in the form of tablets, capsules, gelatine capsules, chew candies, powders to be consumed as such or to be mixed with a liquid before use, syrups, gels, and any other form known to the man skilled in the art. They will contain excipients of suitable formulation, such as colorants, sweeteners, flavourings, bulking agents, binders, preservatives.

These compositions will be able to present themselves in particular in the form of an aqueous, hydroalcoholic or oily solution; an oil-in-water, water-in-oil emulsion or multiple emulsions; they can also present themselves in the form of creams, suspensions, or else powders, suited to an application on the skin, the mucosa, the lips and/or the skin appendages. These compositions can be more or less fluid and have the appearance of a cream, a lotion, a milk, a serum, an ointment, a gel, a paste or a foam. They can also present themselves in solid form, as a stick, or be applied on the skin in the form of an aerosol. They can be used as a care product and/or as a make-up product for the skin.

These compositions further comprise any additive commonly used in the envisaged field of application and also the adjuvants necessary for their formulation, such as solvents, thickeners, diluents, anti-oxidants, colorants, sun filters, self-tanning agents, pigments, charges, preservatives, parfums, odour absorbers, cosmetic or pharmaceutical actives, essential oils, vitamins, essential fatty acids, surfactants, filmogenic polymers, etc.

In all cases, the man skilled in the art will see to it that these adjuvants and also their proportions are selected in such a way as not to prejudice the sought advantageous properties of the composition according to the invention. These adjuvants can, for example, correspond to 0.01 to 20% of the total weight of the composition. When the composition of the invention is an emulsion, the fatty phase can represent from 5 to 80% by weight, and preferably from 5 to 50% by weight with respect to the total weight of the composition. The emulsifiers and co-emulsifiers used in the composition will be selected from those conventionally used in the field concerned. For example, they can be used in a proportion of from 0.3 to 30% by weight, with respect to the total weight of the composition.

The third object of the invention is the use of the active principle in cosmetic or nutraceutical compositions, or for the preparation of pharmaceutical compositions.

Thus, the active principle, owing to its particular properties, will be able to be used in a cosmetic or nutraceutical composition intended to improve the moisturizing and the barrier function of the epidermis or intended to prevent or treat cutaneous dryness.

Moreover, the active principle according to the invention will be able to be used advantageously in a cosmetic or nutraceutical composition intended to combat in a preventive and/or curative manner against the manifestations of cutaneous ageing, and more specifically, so as to combat against and/or to prevent photo-induced ageing (photo-ageing). Cutaneous manifestations of ageing are understood to mean all changes to the exterior appearance of the skin and the skin appendages due to ageing such as, for example, superficial roughness of the stratum corneum, wrinkles and fine lines, but likewise any internal change to the skin which is not systematically expressed by a changed exterior appearance such as, for example, the thinning of the dermis or any other internal degradation of the skin following an exposure to ultraviolet radiation (UV). Thus, the active principle according to the invention, or the composition containing it, will allow a combating, in particular, against the loss of effectiveness of the barrier function of the skin and will allow the regeneration of the dermis and epidermis to be stimulated.

According to another aspect of the invention, the active principle according to the invention will be able to be used advantageously in a cosmetic or nutraceutical composition intended to protect the skin and the mucosa against all types of exterior aggressions.

The expression "exterior aggression" is understood to mean the aggressions which the environment can produce. By way of example, aggressions can be cited such as pollution, UV radiation, or else products of an irritant nature such as surfactants, preservatives or parfums. Pollution is understood to mean both the "exterior" pollution due, for example, to particles of diesel, to ozone or to heavy metals, and also the "interior" pollution, which can be due in particular to solvents of paints, adhesives or wallpapers (such as toluene, styrene, xylene or benzaldehyde), or else cigarette smoke. The dryness of the atmosphere is likewise an important cause of cutaneous desiccation.

The aggressions which the skin and the hair undergo are due, for example, to an imbalance of the electrochemical gradient through the cellular membrane, which can lead to great variations in the osmotic pressure, and this can have as a consequence osmotic shocks and hence the lysing of the cells.

The inventors have now demonstrated, in a surprising manner, that the active principle according to the invention protects the cells against these osmotic shocks.

The skin can likewise be aggressed by treatments such as shaving. Advantageously, the invention has as an object the use in a cosmetic composition of an effective quantity of active principle as previously described, the active principle or the composition containing it being intended to prevent or treat the damage caused to the skin by shaving.

According to another further aspect of the invention, the active principle will be able to be used advantageously in a cosmetic or nutraceutical composition, or to prepare a pharmaceutical composition, intended to stimulate cutaneous regeneration.

The invention likewise has as an object the use in a cosmetic composition, or for the preparation of a pharmaceutical composition, of an effective quantity of active principle as previously described, the active principle, or the composition containing it, being intended to prevent the damage caused to the skin by exposure to the sun or to a desiccating environment.

The invention further consists of the use of the active principle according to the invention for the preparation of a pharmaceutical composition intended to regulate and/or stimulate the activity of aquaporins and to thus prevent or treat the pathologies caused by the dysfunctions of the aquaporins of the skin and of the mucosa, eczema, xerosis, atopic dermitites, buccal, ocular or vaginal dryness.

The invention further consists of a method of cosmetic treatment intended to improve the appearance of the skin or to combat against dryness of the skin and mucosa, according to which an effective quantity of a peptide according to the invention, capable of activating the aquaporin, or a composition containing it, is applied on the areas which are to be treated.

The invention further consists of a method of cosmetic treatment intended to prevent and/or combat against the cutaneous signs of ageing and/or of photo-ageing, according to which an effective quantity of a peptide according to the invention, capable of activating the aquaporin, or a composition containing it, is applied on the areas which are to be treated.

Particular embodiments of this method of cosmetic treatment likewise result from the preceding description. Other advantages and characteristics of the invention will become better apparent on reading the examples, given by way of illustration and being non-restrictive.

EXAMPLE 1

Evaluation of the Protective Effect of the Peptide SEQ ID no4 with Respect to an Osmotic Shock The aim of this study is to determine the protective effect of the peptide SEQ ID no4 with respect to normal human keratinocytes subjected to an osmotic shock caused by sorbitol. The evaluation of the cellular state is then carried out by a viability test by MTT.

Protocol:

Normal human keratinocytes in culture were placed in the presence of the peptide SEQ ID no4 at 0.5%, 1% and 3% from a mother solution at 50 ppm, 24 hours before and during the osmotic shock. The hypertonic culture conditions were realized by adding sorbitol at 250 mM to the culture medium for 24 hours. Non-treated controls are carried out.

Cellular viability tests were then carried out by the MTT technique. The MTT agent (3-[4,5-dimethylthiazol-2-yl]-2,5-diphenyltetrazolium bromide) is used to evaluate the cellular viability. The keratinocytes are incubated in a solution containing 0.1 mg/ml MTT (3-[4,5-dimethylthiazol-2-yl]-2,5-diphenyltetrazolium bromide). This compound is absorbed by the living cells, then metabolized by the mitochondrial enzymes (succinate dehydrogenase) in a blue-violet compound, formazan, which is present in the form of insoluble violet crystals in aqueous medium.

The formazan crystals are solubilized in DMSO. They produce an absorbance (O.D.) proportional to the number of living cells present in the sample. Measurements of absorbance at 540 nm are then carried out. The O.D. is therefore directly proportional to the enzymatic activity and also to the number of living cells.

Results:

The results obtained show in increase in the viability, dependent on dose, of the cells subjected to the osmotic shock when the cells are treated with the peptide SEQ ID no4, in comparison with the non-treated cells. The increase of viability is 12% when the cells are treated with the peptide SEQ ID no4 at 3%.

Conclusions:

The peptide SEQ ID no4 protects effectively the normal human keratinocytes subjected to an osmotic shock.

EXAMPLE 2

Evaluation of the Protective Effect of the Peptide SEQ ID no 5 with Respect to an Induced Cutaneous Dehydration The aim of this study is to determine the protective effect of the peptide SEQ ID no5 with respect to ex vivo epidermis cultures subjected to a stress by an induced cutaneous dehydration.

Protocol:

Biopsies of human skin are relieved of their stratum corneum by stripping by means of an adhesive tape (tape stripping) then held in culture ex vivo, treated with a 1% solution of a mother solution at 50 ppm of peptide SEQ ID no5 for 24 hours. The absence of the stratum corneum induces a high dehydration. Hematoxylin-eosin (H&E) histological sections and stains allow the quality of the cutaneous structures to be evaluated.

Results:

The observation of the sections of skin show a distinct reduction to the signs of cellular stress and a better preservation of the cutaneous structures in the skin biopsies treated by the peptide SEQ ID no 5, compared with the non-treated skin biopsies. Moreover, the appearance of the keratinocytes of the basal layer shows a regenerating effect of the peptide SEQ ID no5.

Conclusions:

The peptide SEQ ID no5 effectively protects the skin from the stress induced by dehydration. Moreover, the peptide SEQ ID no5 allows a regeneration of the epidermis.

EXAMPLE 3

Demonstration of the Activating Effect of the Peptide SEQ ID no5 on the Expression of Claudins and of Keratin K10

The aim of this study is to determine the influence of the peptide SEQ ID no 5 on the expression of claudins and of keratin K10. Claudins are the principal transmembrane proteins of the intercellular adhesion structures known as tight-junction, which play a part in the cellular communication and in epidermal cohesion. Keratin K10 is a specific keratin of the differentiated epidermal layers (stratum granulosum) and is involved in the barrier function of the skin. The quantity of protein was evaluated by immunofluorescence on sections of human skin.

Protocol: Samples of human skin are cultured at the air/liquid interface. A 1% solution of a mother solution at 50 ppm of peptide SEQ ID no5 is applied topically, then the samples are incubated for 24 hours.

These skin samples are then fixed with formaldehyde, then enclosed in paraffin. Sections of 2 to 3 µm are then realized. The immunolabeling is carried out after different stages of washing and of incubation of these sections.

The immunolabeling of claudin-1 is carried out by means of a specific antibody of claudin-1 (claudin-1 antibody: rabbit polyclonal, ref: Ab15098, Abcam, dilution $1/200^{th}$), then a secondary antibody, coupled with a fluorescent marker (alexa Fluor 488 donkey anti-rabbit IgG, A21206, Molecular Probes, $1/1000^{th}$).

The immunolabeling of keratin 10 is carried out by means of a specific antibody of keratin 10 (antibody K10: mouse monoclonal, ref: LHP1, Novocastra, dilution $1/50^{th}$), then a secondary antibody, coupled to a fluorescent marker (alexa Fluor 488 donkey anti-mouse IgG, A21202, Molecular Probes, $1/1000^{th}$).

The skin sections are then examined by epifluorescence microscope (Nikon Eclipse E600 microscope).

Results: The microscopic observations show a stronger fluorescence in the skins treated by the peptide SEQ ID no5 at 1%, in particular the upper layers of the epidermis both for the protein claudin-1 and for keratin K10.

Conclusions: The peptide SEQ ID no5, at the concentration of 0.05 ppm, stimulates strongly the expression of the claudins, in particular in the upper layers of the epidermis. Likewise, the peptide SEQ ID no5, at the concentration of 0.05 ppm, stimulates strongly the expression of keratin K10, and more generally the barrier functions of the epidermis.

EXAMPLE 4

Demonstration of the Stimulating Effect of the Peptide SEQ ID no5 on the Expression of Aquaporins The aim of this study is to determine the influence of the peptide SEQ ID no5 on the expression of aquaporin 3 in samples of skin ex vivo.

Protocol: Samples of human skin are cultured at the air/liquid interface. A 1% solution of a mother solution at 50 ppm of peptide SEQ ID no4 is applied topically, then the samples are incubated for 24 hours or 48 hours.

These skin samples are then fixed with formaldehyde then enclosed in paraffin. Sections of 2 to 3 µm are then realized. The immunolabeling is carried out after different stages of washing and incubation of these sections. The immunolabeling is carried out by means of a specific polyclonal antibody of aquaporin 3 (anti-aquaporin 3 (C-18): goat polyclonal, sc-9885, Santa Cruz, dilution $1/100^{th}$), then a secondary antibody, coupled to a fluorescent marker (alexa-fluor 488 donkey anti-goat Ig G, Molecular Probes, dilution $1/1000^{th}$). The skin sections are then examined by epifluorescence microscope (Nikon Eclipse E600 microscope).

Results: The microscopic observations show a stronger fluorescence in the skins treated by the peptide SEQ ID no4 at 1%, in particular in the upper layers of the epidermis with respect to the non-treated control.

Conclusions: the peptide SEQ ID no 4, at the concentration of 0.05 ppm, stimulates the expression of aquaporin 3, in particular in the upper layers of the epidermis.

EXAMPLE 5

Preparation of Compositions

1—Day Cream

| Commercial names | INCI names | % w/w |
|---|---|---|
| PHASE A | | |
| MONTANOV 68 | Cetearyl Alcohol (and) Cetearyl Glucoside | 5.00 |
| JOJOBA OIL | *Simmondsia Chinensis* (Jojoba) Seed Oil | 3.00 |
| VASELINE OIL | Paraffinum Liquidum (Mineral Oil) | 2.00 |
| SQUALANE | Squalane | 3.00 |
| CERAPHYL 368 | Ethylhexyl palmitate | 4.00 |
| CERAPHYL 41 | C12-C15 Alkyl Lactate | 3.00 |
| RAPITHIX A-60 | Sodium polyacrylate (and) Hydrogenated Polydecene (and) Trideceth -6 | 0.30 |
| PHASE B | | |
| GLYCERIN | Glycerin | 5.00 |
| ALLANTOIN | Allantoin | 0.10 |
| DEMINERALISED WATER | Aqua (Water) | qs 100 |
| PHASE C | | |
| ROKONSAL MEP | Phenoxyethanol (and) Methylparaben (and) Ethylparaben (and) Propylparaben | 0.50 |
| PHASE D | | |
| PEPTIDE SEQ ID n° 5 | | 5 ppm |
| PHASE E | | |
| PARFUM | Parfum (Fragrance) | qs |

Procedure:

Weigh the ingredients of the fatty phase and heat to 70° C. under agitation. Prepare Phase B and heat it to 70° C. Emulsify Phase A in Phase B. Add Phase D towards 50° C. under agitation. Below 40° C., add the active principle (Phase D). Perfume and cool to ambient temperature.

2—W/O Moisturizing Cream

| Commercial names | INCI names | % w/w |
|---|---|---|
| PHASE A | | |
| ARLACEL P 135 | PEG-30 Dipolyhydroxystearate Isononanoate | 2.00 |
| CERAPHYL 375 | Isostearyl Neopentanoate | 3.00 |
| PANALANE L-14E | Hydrogenated Polyisobutene | 3.00 |

-continued

| Commercial names | INCI names | % w/w |
|---|---|---|
| CERAPHYL ODS | Octyldodecyl Stearate | 9.00 |
| CERAPHYL 368 | Ethylhexyl Palmitate | 3.00 |
| PHASE B | | |
| DEMINERALISED WATER | Aqua (Water) | qs 100 |
| ATLAS G-2330 | Sorbeth-30 | 4.00 |
| MAGNESIUM SULPHATE 7 H2O | Magnesium Sulphate | 0.70 |
| PEPTIDE SEQ ID n° 5 | | 3 ppm |
| PHASE C | | |
| LIQUAPAR OPTIMA | Phenoxyethanol (and) Methylparaben (and) Isopropylparaben (and) Isobutylparaben (and) Butylparaben | 0.50 |
| PHASE D | | |
| PARFUM | Parfum (Fragrance) | qs |

Procedure:

Weigh Phase 1 and heat to 75° C. under agitation. Prepare Phase B and heat to 75° C. Emulsify Phase B in Phase A under strong rotor-stator stirring. Homogenize for a few minutes. Cool abruptly by means of a bath of iced water under brisk stirring. Add Phase C at around 50° C. and add the perfume (Phase D) at 40° C. Continue the cooling to room temperature.

3—Moisturizing Lotion

| Commercial names | INCI names | % w/w |
|---|---|---|
| DEMINERALISED WATER | Aqua (Water) | qs 100 |
| GLYCERIN | Glycerin | 2.00 |
| PROPYLENE GLYCOL | Propylene Glycol | 2.00 |
| GLUCAM E-10 | Methyl Gluceth -10 | 1.00 |
| NEOSORB | Sorbitol | 5.00 |
| ALLANTOIN | Allantoin | 0.10 |
| ROKONSAL BSB | Benzoic Acid (and) Sorbic Acid (and) Benzyl Alcohol | 0.30 |
| PEPTIDE SEQ ID n° 4 | | 1 ppm |
| Water-soluble PARFUM | Parfum (Fragrance) | qs |

Procedure:

Incorporate the ingredients one by one to the necessary quantity of water and agitate until perfectly dissolved. Readjust the pH to around 5.5 if necessary. Incorporate the active at the end of formulation. Perfume with a water-soluble perfume under weak stirring.

The invention claimed is:

1. A peptide capable of activating the synthesis of proteins of the family of aquaporins, wherein it corresponds to one of the following sequences

| | |
|---|---|
| (SEQ ID n°1) | Ser-Met-Asn-Pro-Gly-Arg, |
| (SEQ ID n°2) | Gln-Pro-Ala-Lys-Ser, |
| (SEQ ID n°3) | Asn-Pro-Ala-Arg-Asp, |
| (SEQ ID n°4) | Asn-Pro-Ala-Arg, |
| (SEQ ID n°5) | Asn-Pro-Ala-Arg-$NH_2$, |
| (SEQ ID n°6) | Asn-Pro-Ala, |
| (SEQ ID n°7) | Asn-Pro-Ala-$NH_2$, |
| (SEQ ID n°9) | Pro-Ala-Arg-$NH_2$. |

2. The peptide according to claim 1, wherein it corresponds to the sequence SEQ ID no4.

3. The peptide according to claim 1, wherein it corresponds to the sequence SEQ ID no5.

4. A peptide capable of activating the synthesis of proteins of the family of aquaporins, wherein the peptide is selected from the group consisting of

| | |
|---|---|
| Ser-Met-Asn-Pro-Gly-Arg, | (SEQ ID n° 1) |
| Gln-Pro-Ala-Lys-Ser, | (SEQ ID n° 2) |
| Asn-Pro-Ala-Arg-Asp, | (SEQ ID n° 3) |
| Asn-Pro-Ala-Arg, | (SEQ ID n° 4) |
| Asn-Pro-Ala-Arg-$NH_2$, | (SEQ ID n° 5) |
| Asn-Pro-Ala, | (SEQ ID n° 6) |
| Asn-Pro-Ala-$NH_2$, and | (SEQ ID n° 7) |
| Pro-Ala-Arg-$NH_2$, | (SEQ ID n° 9) | wherein the peptide is in a protected form based on either an acylation or an acetylation of the amino-terminal end, either an amidation or an esterification of the carboxy-terminal end, or both.

5. The peptide according to claim 1, wherein the proteins of the family of aquaporins are aquaporins of type 3.

6. A cosmetic or pharmaceutical composition, wherein it contains in a physiologically acceptable medium, as active principle, an effective quantity of a peptide capable of activating the synthesis of proteins of the family of aquaporins and corresponding to one of the following sequences:

| | |
|---|---|
| (SEQ ID n°1) | Ser-Met-Asn-Pro-Gly-Arg, |
| (SEQ ID n°2) | Gln-Pro-Ala-Lys-Ser, |
| (SEQ ID n°3) | Asn-Pro-Ala-Arg-Asp, |
| (SEQ ID n°4) | Asn-Pro-Ala-Arg, |
| (SEQ ID n°5) | Asn-Pro-Ala-Arg-$NH_2$, |
| (SEQ ID n°6) | Asn-Pro-Ala, |
| (SEQ ID n°7) | Asn-Pro-Ala-$NH_2$, |
| (SEQ ID n°8) | Pro-Ala-Arg, |
| (SEQ ID n°9) | Pro-Ala-Arg-$NH_2$, | previously solubilized in one or more cosmetically or pharmaceutically acceptable solvents, selected from the group consisting of water, glycerol, ethanol, propylene glycol, butylene glycol, dipropylene glycol, ethoxylated or propoxylated diglycols, cyclic polyols, petroleum jelly, a vegetable oil or any mixture of these solvents.

7. The cosmetic or pharmaceutical composition according to claim 6, wherein the peptide is present at a concentration comprised between approximately 0.0005 and 500 ppm, and preferably at a concentration comprised between 0.01 and 5 ppm.

8. The cosmetic or pharmaceutical composition according to claim 6, wherein it further contains glycerol as a moisturizing agent.

9. A cosmetic or nutraceutical composition comprising an effective quantity of peptide, alone or in association with another active principle, the peptide being capable of activating the synthesis of proteins of the family of aquaporins and being one of the following sequences:

Ser-Met-Asn-Pro-Gly-Arg, (SEQ ID n° 1)

Gln-Pro-Ala-Lys-Ser, (SEQ ID n° 2)

Asn-Pro-Ala-Arg-Asp, (SEQ ID n° 3)

Asn-Pro-Ala-Arg, (SEQ ID n° 4)

Asn-Pro-Ala-Arg-NH$_2$, (SEQ ID n° 5)

Asn-Pro-Ala, (SEQ ID n° 6)

Asn-Pro-Ala-NH$_2$, (SEQ ID n° 7)

Pro-Ala-Arg-NH$_2$; (SEQ ID n° 9)

and one or more cosmetically or pharmaceutically acceptable solvents selected from the group consisting of water, glycerol, ethanol, propylene glycol, butylene glycol, dipropylene glycol, ethoxylated or propoxylated digylcols, cycle polyols, petroleum jelly, a vegetable oil or any mixture of these solvents;

wherein the composition improves the moisturizing and the barrier function of the epidermis.

10. The cosmetic or nutraceutical composition of claim 9, comprising an effective quantity of peptide as an active principle, alone or in association with another active principle, to treat cutaneous dryness.

11. The cosmetic or nutraceutical composition of claim 9, comprising an effective quantity of peptide as an active principle, alone or in association with another active principle, to stimulate cutaneous regeneration.

12. The cosmetic or nutraceutical composition of claim 9, comprising an effective quantity of peptide as an active principle, alone or in association with another active principle, to treat the cutaneous signs of ageing and/or of photo-ageing.

13. The cosmetic or nutraceutical composition of claim 9, comprising an effective quantity of peptide as an active principle, alone or in association with another active principle, to treat the pathological states linked to dryness of the skin.

14. A method of cosmetic treatment to promote the activity of aquaporins, the method comprising:
applying the cosmetic or pharmaceutical composition of claim 6 topically on the skin to be treated.

15. A method of cosmetic treatment to promote a reduction in cutaneous dryness, the method comprising:
applying the cosmetic or pharmaceutical composition of claim 6 topically on the skin to be treated.

16. The peptide according to claim 4, wherein the proteins of the family of aquaporins are aquaporins of type 3.

17. The cosmetic composition according to claim 7, wherein it further contains glycerol as a moisturizing agent.

18. The method of claim 14, wherein the peptide is present at a concentration comprised between approximately 0.0005 and 500 ppm, and preferably at a concentration comprised between 0.01 and 5 ppm.

19. The method of claim 18, wherein the cosmetic or pharmaceutical composition further contains glycerol as a moisturizing agent.

20. The method of claim 15, wherein the peptide is present at a concentration comprised between approximately 0.0005 and 500 ppm, and preferably at a concentration comprised between 0.01 and 5 ppm.

21. The method of claim 20, wherein the cosmetic or pharmaceutical composition further contains glycerol as a moisturizing agent.

\* \* \* \* \*